Feb. 16, 1971 E. C. CURTIS Plant Pat. 3,027
DISTINCT VARIETY OF ROSE
Filed Dec. 2, 1968
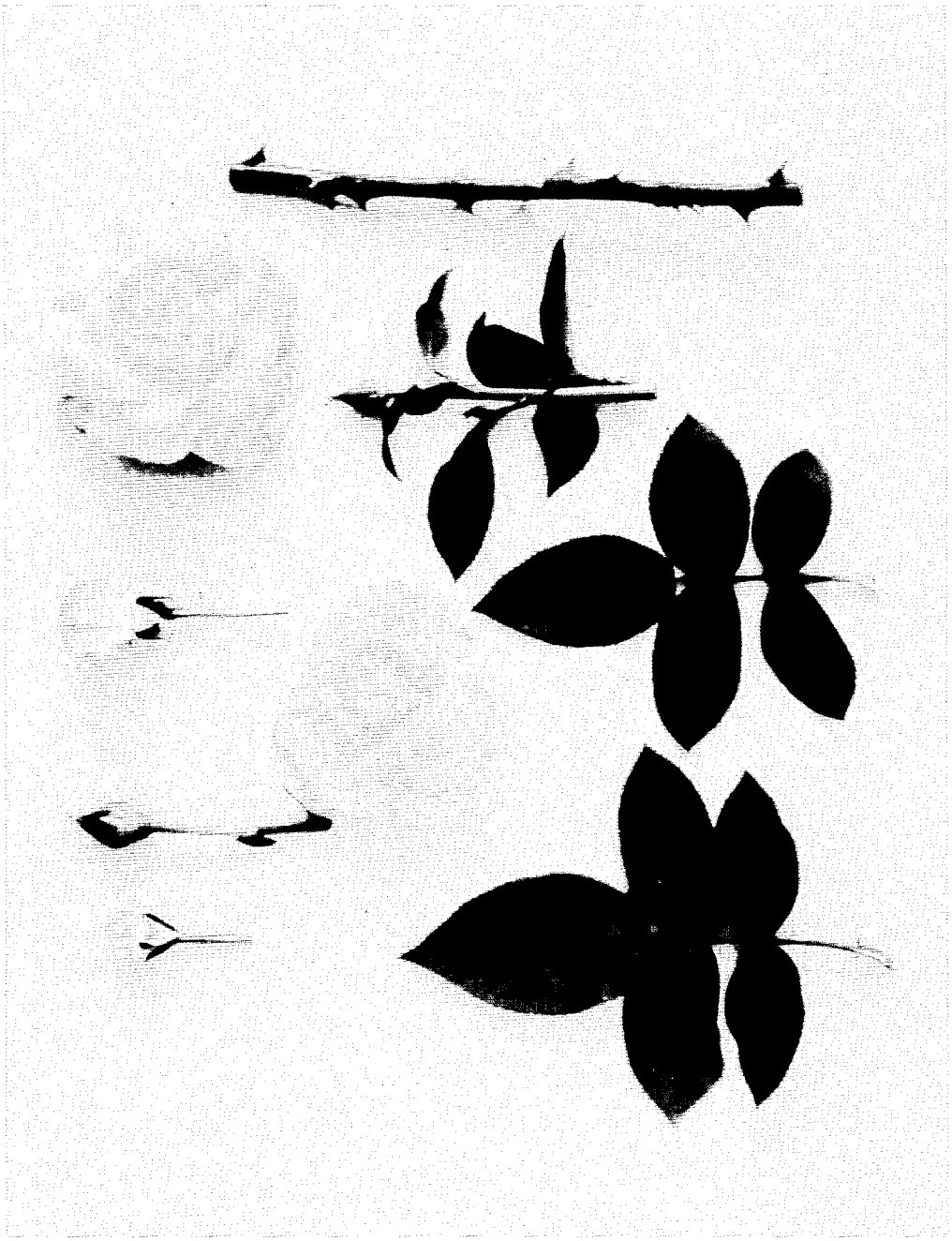

United States Patent Office

Plant Pat. 3,027
Patented Feb. 16, 1971

3,027

DISTINCT VARIETY OF ROSE PLANT

Eldon C. Curtis, Dallas, Tex., assignor to E. V. Kimbrew, Wills Point, Tex.

Filed Dec. 2, 1968, Ser. No. 780,609
Int. Cl. A01h *5/00*
U.S. Cl. Plt.—16 1 Claim

ABSTRACT OF THE DISCLOSURE

A new and distinct variety of hybrid tea rose plant produced by crossing Peace on Hawaii, Plant Pat. No. 1,833.

The present invention relates to a new and distinct variety of rose plant of the hybrid tea class which was originated by crossing Peace (Plant Pat. No. 591) on Hawaii (Plant Pat. No. 1,833). The new and distinct variety was asexually reproduced in Canton, Tex.

This rose differs from its seed parent Peace by being taller and with more upright growth, with blooms not as large but high-centered and of a different color.

This rose differs from its pollen parent Hawaii (Plant Patent No. 1,833) by having a more freely branched plant with branches growing upright and taller; essentially solid blossom color, slightly less brilliant than the inner petal surface of the parent plant.

The accompanying drawing shows typical specimens of the growth and habit of my new variety in different stages of development and in a color as nearly true as is possible to make the same in a color illustration of this character.

The following is a detailed description of my new rose variety with color terminology in accordance with the Horticultural Color Chart of the Royal Horticultural Society except where general color terms of ordinary dictionary significance are used:

Type: Upright bush, seedling, for garden decoration.
Class: Hybrid tea.

THE FLOWER

Locality where grown: Canton, Tex.
Flowers borne: Singly, and a few clusters; strong, good length stems.
Quantity of bloom: Profuse.
Continuity: Throughout growing season.
Fragrance: Mild rose.
Bud:
- *Peduncle.*—Medium length, strong.
- *Before calyx breaks.*—Size: Medium. Form: Ovoid (between pointed and ovoid).
- *As calyx breaks.*—Color: Red 46A.
- *As first petal opens.*—Size: Medium. Form: Medium, ovoid (somewhat pointed). Color: Outside—orange red 33A; inside—orange red 33B. Opening: Opens well.

Bloom:
- *Size when fully open.*—Medium, 4 inches to 5 inches.
- *Petalage.*—40 to 50 petals, regularly arranged.
- *Form.*—Medium.

Petals:
- *Shape.*—Outer: Rounded with point at apex. Intermediate: Ovoid, with point at apex. Inner: Ovoid, with irregular apex.

- *Color.*—Outer petal: Outside surface—orange red 33A; base, yellow orange 16D; inside surface—orange red 33A; base, yellow orange 16C. Intermediate petal: Outside surface—orange red 33C; base, yellow orange 16D; inside surface—orange red 33B; base, yellow orange 16C. Inner petal: Same as intermediate petal; outside surface—same as intermediate petal; inside surface—same as intermediate petal.

This description was made from a rose that was open for three days, outdoors in October 1968, at Canton, Tex.

- *Color.*—Outer petal: outside surface—orange red 33C; base, yellow orange 16D; inside surface—orange red 33C; base, yellow orange 16C. Inner petal: outside surface—same as outer petal; inside surface—same as outer petal.
- *General color effect.*—Newly opened flower: Orange red 32B; three days open—same as new (holds color well).
- *Behavior.*—Drop off cleanly.
- *Flower longevity.*—On bush in field, 7 days in October; useful for 8 days in vase in office.

REPRODUCTIVE ORGANS

Stamens: Medium, arranged regularly about pistils, occasionally mixed with petaloids.
Filaments: Many, medium length. Color: Red 44C.
Anthers: Many, opening normally. Color: Yellow to light red (general color term).
Pollen: Moderate, yellow (general color term).
Pistils: Medium, numerous.
Styles: Red, uneven, loosely bunched.
Stigma: Yellow orange 19C.
Ovaries: Mostly enclosed in receptacle.
Hips: Frequent.
Sepals: Uniformly downward when flower opens.
Seeds: Many.

PLANT

Foliage:
- *Leaves.*—Compound, 3 to 7 leaflets.
- *Leaflets.*—Shape: Ovate with acute apex, serrate.
- *Color.*—Mature: Upper surface—green 137A; under surface—green 138B. Young: Upper surface—greenish red (general color term); under surface—light green red (general color term).
- *Rachis (the supporting stem of the compound leaf).*—Upper side: Hairy. Under side: Smooth.
- *Stipules.*—About ¾ inch long.
- *Disease.*—Resistant; especially to powdery mildew.

Growth:
- *Habit.*—Upright, much branched.
- *Growth.*—Dense.
- *Canes.*—Medium to heavy.
- *Main stems.*—Straight; color—medium green (general term). Prickles: Many; color—greenish red (general term). Hairs: Few color—greenish red (general term).
- *Branches.*—Straight, medium length; color—medium green (general term). Prickles: Many; color—greenish red (general term).
- *Hairs.*—Few. Color: Greenish red.
- *New shoots.*—Conspicuous, attractive; color—reddish purple (general term). Prickles: Some prickles; color—reddish purple (general term). Hairs: Few; color—reddish purple.

I claim:

1. A new and distinct variety of rose plant of the hybrid tea class, substantially as herein shown and described, characterized particularly as to novelty by the combination of a freely branched and upright plant, good blossom color which holds well, disease resistance, especially to powdery mildew, attractive brilliant flowers corresponding to Orange red 32B HCC, and good keeping qualities as cut flowers.

No references cited.

ROBERT E. BAGWILL, Primary Examiner